United States Patent
Tamiya et al.

(10) Patent No.: US 12,411,136 B2
(45) Date of Patent: Sep. 9, 2025

(54) ELECTROCHEMICAL LATERAL FLOW IMMUNOLOGICAL TEST METHOD, SENSOR FOR SAME, AND METHOD FOR MANUFACTURING SAME

(71) Applicants: IMMUNOSENS CO., LTD., Suita (JP); OSAKA UNIVERSITY, Suita (JP)

(72) Inventors: Eiichi Tamiya, Suita (JP); Takenori Shimizu, Saitama (JP); Shigeki Yamada, Suita (JP)

(73) Assignee: IMMUNOSENS CO., LTD., Suita (JP)

( * ) Notice: Subject to any disclaimer, the term of this patent is extended or adjusted under 35 U.S.C. 154(b) by 429 days.

(21) Appl. No.: 17/786,705

(22) PCT Filed: Dec. 15, 2020

(86) PCT No.: PCT/JP2020/046777
§ 371 (c)(1),
(2) Date: Jun. 17, 2022

(87) PCT Pub. No.: WO2021/125173
PCT Pub. Date: Jun. 24, 2021

(65) Prior Publication Data
US 2023/0030862 A1 Feb. 2, 2023

(30) Foreign Application Priority Data
Dec. 18, 2019 (JP) .................. 2019-227844

(51) Int. Cl.
*G01N 33/543* (2006.01)
*G01N 27/327* (2006.01)
*G01N 27/48* (2006.01)

(52) U.S. Cl.
CPC ..... *G01N 33/54388* (2021.08); *G01N 27/327* (2013.01); *G01N 27/48* (2013.01)

(58) Field of Classification Search
None
See application file for complete search history.

(56) References Cited

U.S. PATENT DOCUMENTS

| | | | |
|---|---|---|---|
| 2016/0054311 A1* | 2/2016 | Marks | G01N 33/5438 204/403.01 |
| 2017/0067889 A1 | 3/2017 | Tamir | |

FOREIGN PATENT DOCUMENTS

| | | |
|---|---|---|
| JP | 2001-337065 A | 12/2001 |
| JP | 2006-524815 A | 11/2006 |

(Continued)

OTHER PUBLICATIONS

PCT/ISA/210, "International Search Report for PCT International Application No. PCT/JP2020/046777," Mar. 16, 2021.

*Primary Examiner* — J. Christopher Ball
(74) *Attorney, Agent, or Firm* — HAUPTMAN HAM, LLP

(57) ABSTRACT

In an electrochemical lateral flow immunological test method, flow of a sample solution is controlled. As a result, the reaction time is short and quantitative measurements and electrical measurements can be performed with excellent sensitivity and high accuracy, and the invention provides a sensor employed in the method. Electrode portions, electrically conductive portions for transferring electric current from the electrode portions, and connecting portions connected to an electrical measuring instrument for measuring the electric current values are arranged on a supporting body including a resin sheet, pads and the like disposed by partial lamination on the supporting body. A sample solution flows over the plurality of pads, and electrochemical detection is performed by controlling the flow at the position of the electrode portions. Furthermore, the flow is controlled by a (Continued)

flow rate control pad, a flow passage portion fiber pad, and flow rate control protruding portions.

14 Claims, 5 Drawing Sheets

(56) References Cited

FOREIGN PATENT DOCUMENTS

| | | |
|---|---|---|
| JP | 2009-210417 A | 9/2009 |
| JP | 5187759 B2 | 4/2013 |
| JP | 6714256 B1 | 6/2020 |
| WO | 02-37099 A1 | 5/2002 |

* cited by examiner

Fig. 8 (a) 31-1
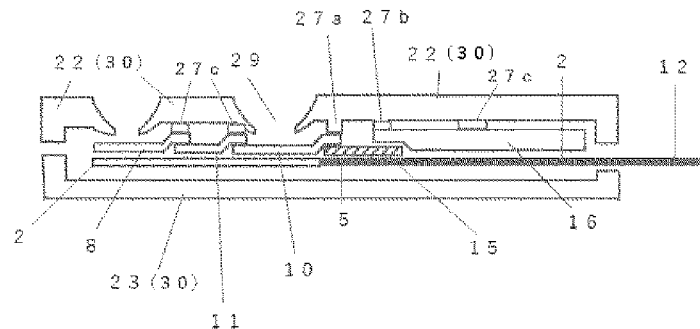
Fig. 8 (b) 31-2
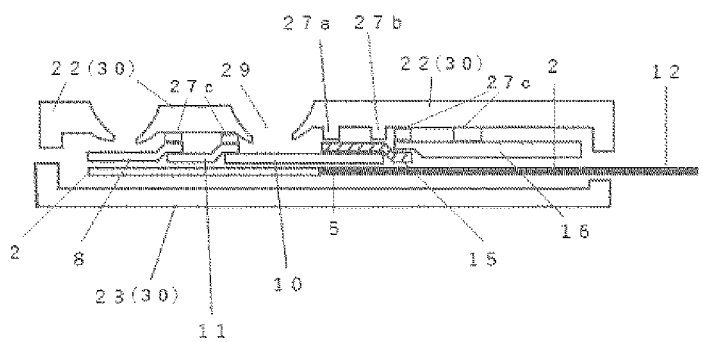
Fig. 9 (a)
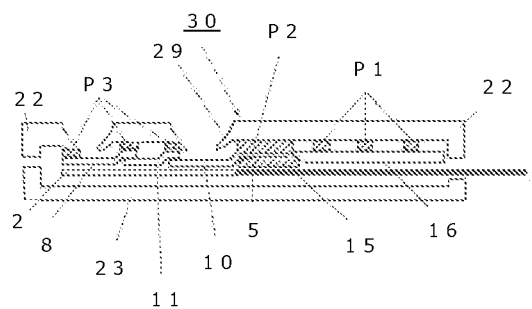
Fig. 9 (b)
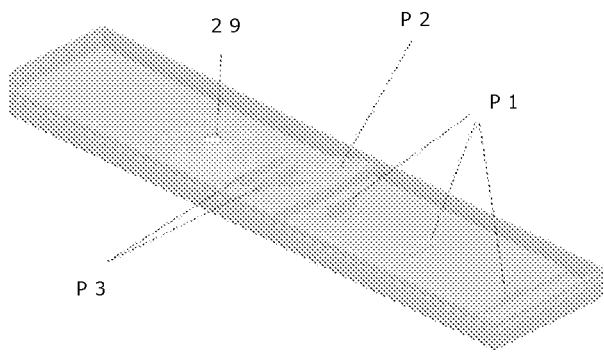

ELECTROCHEMICAL LATERAL FLOW IMMUNOLOGICAL TEST METHOD, SENSOR FOR SAME, AND METHOD FOR MANUFACTURING SAME

RELATED APPLICATIONS

The present application is National Phase of International Application No. PCT/JP2020/046777 filed Dec. 15, 2020, and claims priority from Japanese Application No. 2019-227844, filed Dec. 18, 2019, the disclosure of which is hereby incorporated by reference herein in its entirety.

TECHNICAL FIELD

The present invention relates to an electrochemical lateral flow immunological sensor test method for detecting antigens and antibodies in a body fluid, proteins in a food raw material/processed product, or the like, and to a manufacturing method of the sensor.

BACKGROUND ART

In recent years, "Point of Care Testing" in which specimens are tested during consultation of a patient has become popular in clinics and small-scaled hospitals. Visual determination (qualification) products are distributed for diagnosing organ-specific abnormalities using a blood biochemistry testing system composed of a dry chemistry reagent and a small colorimeter, and for diagnosing infectious diseases using an immunochromatographic test strip for specimens of mucus membrane fluid and blood from pharynx or nose.

The immunochromatographic test strip refers to a method of detecting a test substance to be detected in a sample by an antigen-antibody reaction. In the immunochromatographic test strip: an antibody or antigen against an antigen or antibody as a test substance is immobilized on an insoluble membrane carrier as a chromatographic medium to prepare a detection portion as a stationary phase; the detection portion is used as a mobile phase including a marker which is a conjugate (detection reagent) bonded with an antibody or antigen bondable with the aforementioned detection substance; the test substance is specifically reacted with the conjugate as the mobile phase; and furthermore, on the detection portion as the stationary phase, the test substance bonded with the conjugate is specifically reacted with the antibody or antigen immobilized on the detection portion. Since colloidal metal particles such as gold colloids or colored latex particles are usually used as a marker, the presence of the test substance in the sample is detected on the basis of the color on the detection portion. As described in Patent Document 1, the immunochromatographic test strip is generally configured so as to include: a sample pad for feeding a sample; a conjugation pad for arranging a conjugate as a mobile phase; an insoluble membrane carrier for developing a complex of the sample and the conjugate and having a detection portion for detection; and an absorption pad for absorbing the sample that has developed the insoluble membrane carrier.

In Patent Document 2, the inventor of the present invention discloses a method (measurement method of a test substance), including: preparing a working electrode on which a first antibody specifically bondable with a test substance is immobilized and metal particles as a marker to which a second antibody specifically bondable with the test substance; feeding an antigen or antibody as the test substance and an antibody or antigen bonded to the marker onto a surface of the working electrode so as to cause an antigen-antibody reaction, thereby gathering the metal particles in an amount corresponding to that of the test substance in a sample solution near the face of the working electrode; controlling a potential of the working electrode so as to electrochemically oxidize the metal particles and removing the unreacted metal particles bonded with the second antibody after dripping an aqueous chloride solution of NaCl, KCl or HCl (which also serves as a washing solution to remove the marker bonded with an electrolytic solution and the unreacted antibody or antigen) to the working electrode, thereby making a state where influence of noises resulting from the antibody and antigen for the measurement as well as contaminants in a measurement solution is suppressed; measuring an electric current value generated in electrochemically reducing the metal fine particles that have been oxidized in the state of suppressed noises; and examining the presence or a concentration of the test substance on the basis of the electric current value.

Patent Document 2 describes " . . . the strip and the printed electrode are superimposed so that the working electrode of the printed electrode comes into contact with the determination portion", " . . . includes an absorption pad 25 and a backing sheet 26 disposed on the rear face side of the membrane 22. As illustrated in FIG. 4 (*a*), primary antibodies 2 are immobilized on a predetermined area of the surface of the membrane 22 to form a determination portion (immobilization area) 23. On the surface of the membrane 22 downstream of the determination portion 23, antibodies specifically bondable with the secondary antibodies 4 labeled with the metal fine particles 5 are immobilized to form a control portion 24.", and further describes "At least the determination portion 23 of the membrane 22 and the working electrode 1 are superimposed.", "after superimposing at least the determination portion 23 of the membrane 22 and the working electrode 1", and "the strip and the printed electrode were superimposed so that the working electrode of the printed electrode as illustrated in FIG. 6 is in contact with the determination portion". However, as a result of verification according to this Patent Document 2, at the position of the electrode portion, a percentage of the test substances showing no antigen-antibody reaction in the sample solution is high, and therefore it can be said that the test substance in the sample solution could not be correctly quantified.

PRIOR ART DOCUMENTS

Patent Documents

Patent Document 1: WO 2002037099A1
Patent Document 2: Japanese Patent No. 5187759

SUMMARY OF INVENTION

Problem to be Solved

However, the conventional immunochromatographic test strip refers to a method in which a hue generated by a reaction of a capture antibody applied in a linear pattern to a detection portion on a surface of an insoluble membrane carrier and an antibody bonded to a marker with an antigen in a test solution is and qualitatively evaluated by visual determination or semi-quantitatively measured using an apparatus including an optical system. This method has a problem that it is difficult to accurately and precisely determine the amount of the test substance. Therefore, it is desirable to enable prompt and accurate quantitative test using a smaller and portable measuring instrument.

As can be seen the above verification, in Patent Document 2, it is impossible to achieve an accurate measurement without controlling a flow rate, a flow pattern, and a flow volume at the position of the electrode portion, and the configuration does not allow easy connection to the measuring instrument and prompt measurement. Furthermore, the manufacture method of such a measuring instrument (sensor) was not considered.

In addition, it is undesirable to use an adhesive for fixing pads. In principle, an adhesive cannot be used particularly in the electrode portion (working electrode, counter electrode, working electrode) because an antigen (or antibody) in a sample solution that has reacted with an antibody (or antigen) bonded to a gold colloid cannot react with an antibody (or antigen) immobilized on the electrode (working electrode). It has been a very difficult problem that a minimum flow rate and time necessary for the antigen-antibody reaction are ensured so as to cause the sample solution to steadily flow over the surface of the electrode portion without using any adhesive or the like when pads are placed on the electrode portion.

Thus, an object of the present invention is to provide an electrochemical lateral flow immunological test method that enables quantitative and electrical measurements with short reaction time, excellent sensitivity, and high accuracy by controlling a flow of a sample solution, and to provide a sensor for the method. Also, an object of the present invention is to provide a manufacturing method with low cost, in which the sensor can be mass-produced by utilizing a pre-existing manufacturing facility, for the purpose of efficiently mounting pads of a pre-existing immunochromatographic test strip on a supporting body on which an electrode portion is printed. Furthermore, an object of the present invention is to provide a lateral flow immunosensor and a manufacturing method thereof, in which, when the pads are placed on the supporting body on which the electrode portion is printed, pads can be fixed using no adhesive so as to cause the sample solution to steadily flow over the electrode portion.

Solution to Problem

In the present invention, it is preferable that a flow rate control pad is provided on each of the aforementioned electrode portions so as to cause the sample solution to flow at an appropriate speed for obtaining a necessary minimum reaction time when the sample solution of the test substance moves to the electrode portion through the flow passage portion fiber pad and the test substance in the sample solution comes into close contact with the electrode portion, and so as to complete the antigen-antibody reaction (sandwich method) on the working electrode.

According to the present invention, the flow rate control pad is placed corresponding to the position of the electrode portion on the supporting body composed of a resin sheet so that the flow of the sample solution at the position of the electrode portion can be controlled to ensure a necessary minimum reaction time, and the sensitivity at the electrode portion can be improved, resulting in a prompt, simple and accurate quantitative measurement. That means, by providing the flow rate control pad, the flow of the sample solution at the position of the electrode portion can be controlled, and the flow of the sample solution can be controlled to the minimum reaction time and rate required for the antigen-antibody reaction of the sample solution flowing over the pads near the electrode surface, so that a micro flow passage, a pump, and the like for the above-mentioned flow rate control can be omitted. Therefore, a prompt and simple quantitative measurement with high sensitivity can be achieved using a portable small-scaled electric current meter. In such a way, the flow pattern is controlled near the electrode surface such that the flow is in close contact with the electrode portion while the volume and the flow rate of the sample solution is kept constant on the electrode surface.

The sample pad, the conjugation pad, the absorption pad, and the supporting body in the lateral flow immunosensor according to the present invention can be manufactured using the same materials as for the sample pad, the conjugation pad, and the absorption pad used for a general immunochromatographic test strip as described in Patent Document 1.

However, unlike pre-existing immunochromatographic test strips, the lateral flow immunosensor according to the present invention is manufactured by partially laminating the sample pad, the conjugation pad, the flow passage portion fiber pad, the flow rate control pad, and the absorption pad onto the supporting body on which an electrode described below is printed. With respect to the pads, the conjugation pad is partially laminated on the upstream upper face of the flow passage portion fiber pad, and the flow rate control pad is partially laminated on the downstream lower face of the flow passage portion fiber pad or laminated on the upper face of the electrode portion on which the flow passage portion fiber pad is placed. The flow passage portion fiber pad and the flow rate control pad are made of materials different from those for general immunochromatography.

The present invention is characterized in that the flow passage portion fiber pad different from that in the general immunochromatography is in contact with a part of the downstream lower face of the conjugation pad, and the flow rate control pad for completing the antigen-antibody reaction (sandwich method) on the working electrode is in contact with a part of the downstream lower face of the flow passage portion fiber pad and placed on the upper face of the aforementioned electrode portion. Preferably, the flow passage portion fiber pad is provided which has a function of moving the sample solution to the electrode portion during the immunological reaction in the conjugation pad in which an antibody or antigen immunologically reactive with the antibody or antigen in the sample solution is bonded to colloidal metal particles such as gold, and infiltrated into the pad and dried.

According to the present invention, the flow rate control pad controls the flow rate of the sample solution for a necessary minimum reaction time for the antigen-antibody reaction, thereby enabling to promptly and accurately perform the electrical detection on the working electrode.

To feed the electrolytic/washing solution onto the flow passage portion fiber pad, an electrolytic/washing solution hole can be formed on an upper case 22. By feeding the electrolytic/washing solution from the top of the flow passage fiber pad, unreactants can be washed more efficiently.

In the electrochemical lateral flow immunosensor according to the present invention, even if the electrolytic/washing solution is fed from the sample hole, the unreactants can be washed and measurement results without much difference can be obtained.

For the present invention, in the electrochemical lateral flow immunosensor, it is preferable that the antibody or antigen immunochemically reactive with the test substance bonded to the marker is different from the antibody or antigen immunochemically reactive with the test substance immobilized on the surface of the working electrode. That means, it is preferable that the antibody or antigen immunochemically reactive with the test substance bonded to the marker and the antibody or antigen immunochemically reactive with the test substance immobilized to the surface of the working electrode individually recognizes different sites of the test substance. The use of different antibodies or antigens for the marker and the working electrode improves the specificity and sensitivity. Antibodies used for research or as raw materials of a product include polyclonal antibodies and monoclonal antibodies, which differ from each other in production methods and properties and are therefore individually used depending on intended purposes. Monoclonal antibodies can bind to only one recognition site (epitope) of a target protein. On the other hand, polyclonal antibodies can bind to a plurality of epitopes of the same protein, and therefore one polyclonal antibody can recognize a plurality of epitopes of a protein.

Preferably, the present invention includes a cassette case for accommodating the electrochemical lateral flow immunosensor, and the cassette case includes a flow rate control protruding portion that presses the flow rate control pad from above so as to control the flow by damming up. The aforementioned object can be achieved whether a plurality or one of the flow rate control protruding portions press a part or the whole of the flow rate control pad from above.

According to the present invention, the flow rate control protruding portion placed on the cassette case presses the flow rate control pad placed on the electrode portion from two position of upper side and lower side for damming up the flow so as to ensure a minimum flow rate and flow time required for the antigen-antibody reaction and to cause the sample solution to steadily flow over the surface of the electrode portion.

Preferably, the present invention also includes a cassette case for accommodating the electrochemical lateral flow immunosensor. The connecting portion is protruded outward from the cassette case, plugged into an electrical measuring instrument for detecting an electric current of the electrode portion, and connected to an electrical circuit of the electrical measuring instrument to measure an electric current generated on the electrode.

According to the present invention, while the lateral flow immunosensor is accommodated inside the cassette case, the connecting portion protruding outside the cassette case can be plugged into the electrical measuring instrument for detecting the electric current of the electrode portion, thereby the electrical circuit can be constructed to promptly measure the electric current generated on the electrode.

For the present invention,
The electrochemical lateral flow immunosensor attached to a cassette case according to claim 14, wherein:
the electrode portion, an electrically conductive portion for transferring an electric current from the electrode portion, and a connecting portion connected to an electrical measuring instrument for measuring a value of the electric current from the electrode portion, are placed on a supporting body composed of a resin sheet;
on the the electrode portion of the resin sheet, the flow rate control pad is provided over a surface of the electrode portion on the support body or provided on an upper surface of the electrode portion of the flow passage portion fiber pad which is placed up to the upper face of the electrode portion; and
an upstream side and a downstream side of the flow rate control pad are pressed from above with a moderate pressure by the flow rate control protruding portion so as to control the flow pattern including the flow rate and/or volume of the sample solution in a predetermined area of the flow rate control pad.

The electrochemical lateral flow immunosensor attached to a cassette case according to claim 14, wherein:
a strip and the printed electrode are superimposed on the supporting body composed of the resin sheet such that the printed electrode as the working electrode of the electrode portion is in contact with the flow rate control pad;
the flow rate control protruding portion on an upstream side is placed on the working electrode of the electrode portion;
the flow rate control protruding portion on a downstream side is placed on the counter electrode (or reference electrode) of the electrode portion; and
an area between the upstream flow rate control protruding portion and the downstream flow rate control protruding portion that press the flow rate control pad is defined as a reaction area so as to control the flow pattern including the flow rate and/or flow volume of the sample solution.

It is preferable that the flow rate control pad is placed over the surface of the electrode portion on the supporting body or placed on the upper face of the electrode area of the flow passage portion fiber pad placed up to the upper face of the electrode portion, and the flow rate control protruding portion presses the upstream side and the downstream side of the flow rate control pad from above with a moderate pressure so as to control the flow pattern including the flow rate and/or volume of the sample solution in a predetermined area of the flow rate control pad.

According to the present invention, the lateral flow immunosensor can be more efficiently manufactured by: a step of printing silver/silver chloride on an electrical wiring structure and a conductive carbon on the supporting body compose of the resin sheet using a printing technique such as a conventional screen printing; a step of immobilizing the antibody or antigen on the face of the working electrode; and a step of laminating the plurality of pads on the supporting body using a conventional apparatus.

According to the present invention, when the flow rate control pad is placed corresponding to the electrode portion position on the supporting body composed of the resin sheet, the flow of the sample solution at the electrode portion position can be controlled to ensure a necessary minimum reaction time, and the sensitivity on the electrode portion is improved, resulting in a prompt, simple and accurate quantitative measurement. That means, by providing the flow rate control pad, the flow of the sample solution at the electrode portion position can be controlled, and the flow of the sample solution can be controlled to the minimum reaction time and rate required for the antigen-antibody reaction of the sample solution flowing over the pads near the electrode surface, so that a micro flow passage, a pump, or the like for this flow rate control can be omitted. Therefore, a prompt, simple and accurate quantitative measurement with high sensitivity can be achieved using a portable small-scaled electric current meter.

The present invention relates to an electrochemical lateral flow immunosensor that includes: a counter electrode obtained by printing a conductive carbon on a supporting body composed of a resin sheet so as to be opposite to a working electrode obtained by printing a conductive carbon; a reference electrode obtained by printing silver/silver chloride; an electrically conductive portion for transferring each electric current generated from these electrode portions obtained by printing the conductive carbon; and a connecting portion for transferring the electric currents generated from these electrode portions to an electrical measuring instrument, and is characterized in that a plurality of pads are placed on the electrodes on the supporting body to cause a sample solution to flow over the plurality of pads, and the flow is controlled at the electrode portion position for electrochemical detection.

According to the present invention, an accurate electrical measurement can be achieved by ensuring a sufficient antigen-antibody reaction time by controlling the flow of the sample solution at the positions of the three electrode portions.

Preferably, the present invention include a step of placing, on the supporting body: a sample pad that absorbs a dripped sample solution; a conjugation pad that absorbs the sample from the sample pad, and simultaneously dissolves an antibody or antigen bonded to a gold colloid infiltrated in the pad, thereby conjugating the sample with the antibody or antigen; a flow passage portion fiber pad that transfers the antibody or antigen in the sample and the antibody or antigen bonded to the gold colloid toward a working electrode while reacting them; a flow rate control pad that causes an antigen/antibody reaction of the transferred reactant with a capture antibody immobilized on the working electrode to form a sandwich structure; and an absorption pad that absorbs a reaction residue liquid of the sample solution.

Additionally, the present invention is characterized in that, from the upstream side: the lower face of the sample pad excluding a part of a distance where the conjugation pad is laminated is fixed with an adhesive on the supporting body; the conjugation pad is laminated with a part of the upstream upper face of the flow passage portion fiber pad, the remaining part of the lower face is fixed with an adhesive on the supporting body; a part of the flow passage portion fiber pad excluding a part to be laminated with a part of an upstream upper face of the flow rate control pad is laminated with the electrode, the remaining part of the lower face is fixed with the adhesive on the supporting body; the flow rate control pad is in contact with the working electrode, counter electrode, and reference electrode portions (but not fixed with the adhesive on the supporting body) and located on a part of the most upstream part of the electrically conductive portion on which an electrically insulating portion is printed from above, an lower face thereof is fixed with the adhesive on the electrically conductive portion on which an electrical insulator is printed from above, or alternatively the flow passage portion fiber pad is located up to the surface of the electrode portion and the lower face thereof excluding the electrode portion is fixed with the adhesive, the electrode portion is laminated (not fixed with the adhesive), the flow rate control pad is laminated on the upper face of the electrode portion, the downstream lower face beyond the flow rate control pad is fixed with an adhesive on the supporting body, the absorption pad is laminated on a part of the downstream upper face of the flow rate control pad and located up to the downstream end, and the lower face of the absorption pad is fixed with the adhesive on the supporting body where the insulator is printed on the electrically conductive portion.

An electrochemical lateral flow immunosensor attached to a cassette case, wherein: the cassette case for accommodating the electrochemical lateral flow immunosensor is provided, and the electrochemical lateral flow immunosensor is set in the cassette case, the electrochemical lateral flow immunosensor comprising an electrode portion for detecting antigens and antibodies in a body fluid, proteins in a food raw material/processed product, or the like; the electrode portion and a flow rate control pad which controls a flow pattern including a flow rate and/or volume of a sample solution are provided on a supporting body composed of a resin sheet; an absorption pad which absorbs a reaction residue liquid of the sample solution, and a flow passage portion fiber pad which transfers an antibody or antigen bonded to a marker of the sample solution to the flow rate control pad while reacting them; and a flow rate control protruding portion pressing the flow rate control pad, the flow passage portion fiber pad, the sample pad, the conjugation pad, and/or the absorption pad from above so as to control a flow is provided with the cassette case, thereby fixing the pads.

The method for manufacturing the lateral flow immunosensor according to the present invention is characterized in that a flow rate control pad that controls a flow pattern including a flow rate and/or flow volume of a sample solution, an absorption pad that absorbs a liquid of reaction residue in the sample solution, and a flow passage portion fiber pad that moves an antibody or antigen bonded to a marker in the sample solution while reacting them are placed on a supporting body composed of a resin sheet, and a flow rate control protruding portion is provided for fixing the pads, the flow rate control protruding portion pressing the flow rate control pad, the flow passage portion fiber pad, and/or the absorption pad from above so as to control the flow by damming up the flow.

The electrochemical lateral flow immunosensor attached to a cassette case according to claim 14, wherein: the electrode portion, an electrically conductive portion for transferring an electric current from the electrode portion, and a connecting portion connected to an electrical measuring instrument for measuring a value of the electric current from the electrode portion, are placed on a supporting body composed of a resin sheet; on the the electrode portion of the resin sheet, the flow rate control pad is provided over a surface of the electrode portion on the support body or provided on an upper surface of the electrode portion of the flow passage portion fiber pad which is placed up to the upper face of the electrode portion; and an upstream side and a downstream side of the flow rate control pad are pressed from above with a moderate pressure by the flow rate control protruding portion so as to control the flow pattern including the flow rate and/or volume of the sample solution in a predetermined area of the flow rate control pad.

According to the present invention, by the flow rate control protruding portion that pressed the pads from above so as to control the flow by damming up the flow, the pads can be fixed without using any adhesive or the like.

As the manufacture method, the sensor can be more efficiently manufactured by a method in which the plurality of pads are previously prepared together (pads are previously connected to each other) and then collectively stuck to the electrode layer, or the like.

It is also preferred that the cassette case be provided with flow control protrusions that hold the flow control pads, channel section fiber pads, sample pads, conjugation pads, and/or absorption pads from above for positioning the pads, warping, and fixing the stacked sections.

Effects of Invention

According to the present invention, by the flow rate control protruding portion that pressed the pads from above so as to control the flow by damming up the flow, the pads can be fixed without using any adhesive or the like. Even when the pads are placed on the supporting body where the electrode portion is printed, the sample solution can steadily flow over the electrode portion. In addition, the flow pattern including the flow rate and/or flow volume of the sample solution can be controlled by forming the flow rate control protruding portion in accordance with the shape of the electrode portion.

Using the manufacture method of the electrochemical lateral flow immunosensor according to the present invention, automated manufacture with a pre-existing manufacturing facility can be achieved, and products with uniform performance can be obtained. As the manufacture method, the products can be more efficiently manufactured by a method in which the plurality of pads are previously connected to each other and then collectively stuck to the electrode layer, or the like.

BRIEF DESCRIPTION OF DRAWINGS

FIG. 2 (a) illustrates an example in which the flow rate control pad is placed on an electrode portion, and FIG. 2 (b) illustrates an example in which the flow rate control pad is placed on the electrode portion via the flow passage portion fiber pad.

FIG. 3 (a) is a top view of the upper case, and FIG. 3 (b) is a rear view of the accommodation cassette case. A sample hole is indicated by 28, and a washing/electrolytic solution hole is indicated by 29. In the rear view of the upper case, flow rate control protruding portions are indicated by 27, and two of the protruding portions on front side and rear side are illustrated. FIG. 3 (c) is a three-dimensional view of each of the upper face of the upper case, the back face of the upper case, and the upper face of the lower case.

FIG. 6 (a) illustrates an example in which the immunosensor according to the present invention is connected to a portable small-scaled apparatus by plugging the connecting portion of the immunosensor into the portable small-scaled apparatus to measure a reduction current, and FIG. 6 (b) illustrates a configuration of an electrical circuit.

FIG. 7 shows that, once a specimen is dripped onto the sample pad, an antibody bonded with a gold colloid infiltrated in the conjugation pad and dried is dissolved and flows in a lateral direction while causing an antigen-antibody reaction with an antibody in the specimen, and causes an antigen-antibody reaction with a capture antibody immobilized on the electrode (working electrode) to form a sandwich structure, so that the gold colloid in an amount corresponding to the antigen amount in the specimen can be captured.

FIG. 8 is a diagram illustrating an example in which the plurality of pads in the electrochemical lateral flow immunosensor according to the embodiment are pressed from above.

FIG. 9 is a diagram illustrating an example in which the plurality of pads in the electrochemical lateral flow immunosensor according to the embodiment are pressed from above.

DESCRIPTION OF EMBODIMENTS

Embodiments to which the present invention is applied will be described in detail below with reference to the figures.

Figure 1:
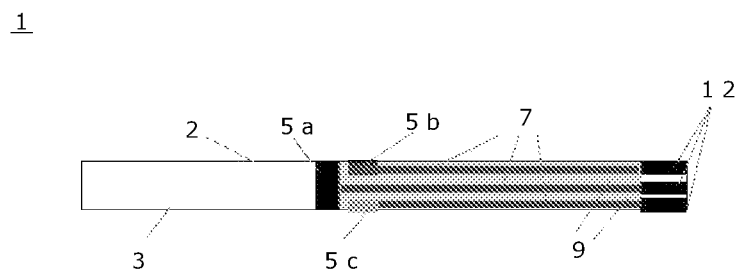
FIG. 1 is a plan view illustrating that, in an electrochemical lateral flow immunosensor according to an embodiment of the present invention, an electrically conductive carbon is printed on an electrode, an electrically conductive portion, and a connecting portion, and an electrical insulator is printed on the electrically conductive portion.
Figure 2:
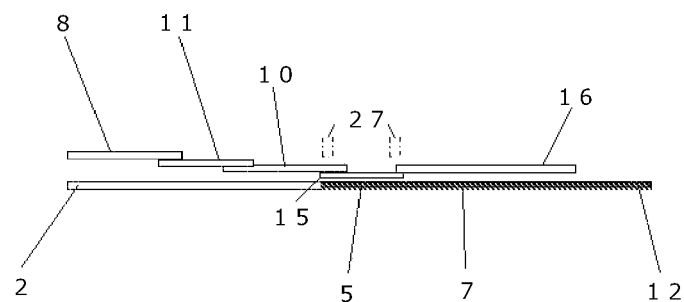
FIG. 2 is sectional views illustrating a laminated structure of pads in the electrochemical lateral flow immunosensor according to the embodiment, in which a part of each of a sample pad, a conjugation pad, a flow passage portion fiber pad, a flow rate control pad, and an absorption pad is laminated with each other in this order from upstream.
Figure 2:
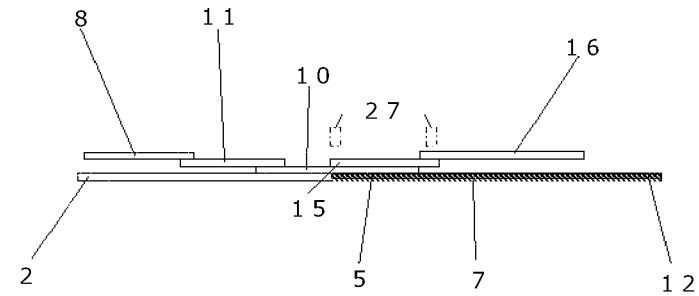

An electrochemical lateral flow immunosensor 1, 2-1, or 2-2 according to the present invention quantifies a test substance by a process in which, as illustrated in FIG. 2 (a) and (b), a sample that potentially contains the test substance is developed in a lateral direction (lateral flow) on a supporting body 2 obtained by printing an electrode on a carrier 3 composed of a resin sheet as illustrated in FIG. 1.

In the sensor 1, 2-1, or 2-2, an electrode portion 5, electrically conductive portion 7 for transferring electric current from the electrode portion 5, and a connecting portion 12 connected to an electrical measuring instrument (meter) 4 for measuring a value of this electric current are placed on the carrier 3 composed of the resin sheet, and pads 8, 10, 11, 15, and 16 are partially laminated with each other on the supporting body. A flow which causes a sample solution to infiltrate over the plurality of pads is controlled at the position of the electrode portion 5 for electrochemical detection. There are two different arrangements indicated by symbols 2-1 and 2-2 in FIG. 2. FIG. 2 (a) illustrates an example in which the flow rate control pad 15 is placed on the electrode portion 5, and FIG. 2 (b) illustrates an example in which a flow rate control pad 15 is placed on the electrode portion 5 via the flow passage portion fiber pad 10.

Figure 5:
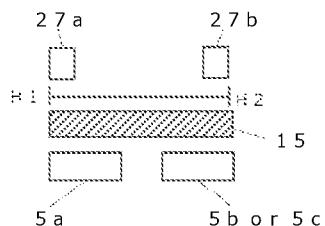
FIG. 5 is a diagram illustrating a positional relationship between the flow rate control protruding portions and the electrode portion on the back face of the cassette in the lateral flow immunosensor according to the embodiment.
Figure 5:
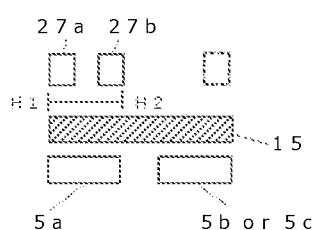
Figure 6:
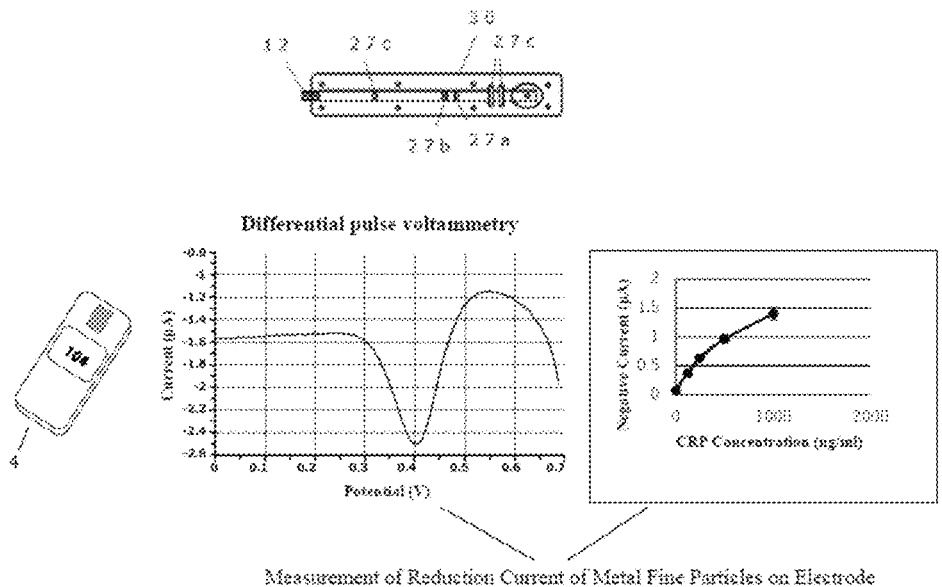
FIG. 6 is a diagram illustrating a usage example of the lateral flow immunosensor according to the embodiment.
Figure 6:
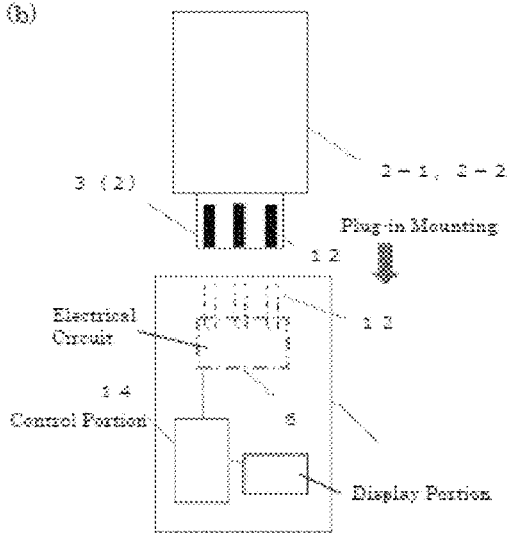

In a method for measuring a test substance using the electrochemical immunosensor according to the present invention, as illustrated in FIG. 1, FIG. 5, and FIG. 6, a working electrode 5a on which a first capture antibody or antigen specifically bondable with the test substance is immobilized and metal particles (marker) bonded with a second antibody or antigen specifically bondable with the test substance are prepared, a test solution and the marker are fed to a surface of the working electrode 5a to cause an antigen-antibody reaction, thereby the metal particles in an amount corresponding to the test substance in a sample solution are gathered near the surface of the working electrode 5a. Then, a potential of the working electrode 5a is controlled to electrochemically oxidize the metal particles, furthermore the metal particles bonded with the unreacted second antibody is removed after causing an aqueous chloride solution of NaCl, KCl or HCl (which serves as both an electrolytic solution and washing solution) to flow in a lateral direction over the working electrode 5a, thereby making a state where influence of noises resulting from the antibody and antigen for the measurement as well as contaminants in a measurement solution is suppressed. In the state of suppressed noise, a reduction current value generated in electrochemically reducing the oxidized metal fine particles is measured to quantify the presence or a concentration of the test substance on the basis of the electric current value.

In the lateral flow immunosensor 1, the sample pad 8, the conjugation pad 11, the absorption pad 16, and the supporting body 2 can be manufactured using the same materials as for a sample pad, a conjugation pad, and an absorption pad used for a general immunochromatographic test strip as described in Patent Document 2. In an immunochromatographic immunoassay, the sample moves through the device by infiltration due to capillary force and binds to a primary antibody that has been previously infiltrated into the conjugation pad 11 to form a conjugate. Then, the conjugate binds to a secondary antibody immobilized as a determination line on a membrane, where the conjugate is captured. The primary antibody that has not been bound to the sample passes through the determination line and flow to a subsequent control line, where the primary antibody is captured. As the principle of the bond, in addition to the sandwich assay, an inhibition assay is also used. Since the lateral flow immunoassay according to the present invention requires a plurality of functions, a plurality of different components should be combined. Although the sample pad 8, the conjugate release pad 11, a reaction membrane, and the absorption pad 16 are typically required, the flow passage portion fiber pad 10 and the flow rate control pad 15 are required, and in some applications, a blood cell separation filter may be required. In this embodiment, the absorption pad 16 and a backing sheet placed on a rear face side of the reaction membrane are provided. The primary antibody is immobilized on a predetermined area of the membrane surface to form an immobilization area (determination portion), and an antibody specifically bondable with the secondary antibody labeled with metal fine particles is immobilized on a surface of the membrane downstream of the determination portion, which can be configured as a control portion (flow rate control pad 15). That means, in the reaction membrane, at least the determination portion and the working electrode 5a are superimposed, and then the strip and the printed electrode 5 are superimposed such that the working electrode 5a of the printed electrode 5 is in contact with the determination portion.

The electrochemical lateral flow immunosensor 2-1 or 2-2 according to this embodiment can be manufactured in such a way that electrodes and wirings are formed on a carrier composed of a synthetic resin sheet via an electrical insulator to form a supporting body having an electrical structure, on which the same materials as for the sample pad 8, the conjugation pad 11, and the absorption pad 16 which are used for a general immunochromatographic test strip are placed (FIG. 2).

However, unlike the pre-existing immunochromatographic test strip, the electrochemical lateral flow immunosensor 2-1 or 2-2 according to the present invention is manufactured in such a way that the sample pad 8, the conjugation pad 11, the flow passage portion fiber pad 10, the flow rate control pad 15, and the absorption pad 16 are partially laminated on the supporting body 2 in which the carrier 3 is coated with the electrode portion 5 by printing or the like. Note that the sample pad 8 and the conjugation pad 11 are placed on the supporting body 2 on which carbon or silver/silver chloride is not printed or which is not coated with carbon or silver/silver chloride.

The method according to the present invention include a step of printing silver/silver chloride on a conductive carbon on a reference electrode 5c and a step of immobilizing an antibody or antigen on the surface of the working electrode 5. The working electrode 5a of the electrode portion 5 is formed over the whole width of the supporting body 2 composed of the resin sheet, and the reference electrode 5c and a counter electrode 5b are placed on the left end side and the right end side respectively of the supporting body 2 on the rear side (downstream side) of the working electrode 5a. Each of the electrode portions 5a, 5b, and 5c is drawn out from the electrically conductive portion 7 and connected to the connecting portion 12 on the rear downstream side. The connecting portion 12 is plugged into the electrical measuring instrument 4 (the connecting portion 12 is also exposed from a cassette case 31-1 or 31-2), so that an electrical measurement is performed by the electrical measuring instrument 4 (FIG. 5).

(Electrode Portion Printed on Supporting Body)

As illustrated in FIG. 1 and FIG. 2, the conductive carbon in a shape indicated by blackening in the figure is printed on the supporting body 2 composed of the synthetic resin sheet to form bases of the working electrode 5a, the reference electrode 5c and the counter electrode 5b, the electrically conductive portion 7 for transferring electric current, and the connecting portion 12 for connecting to the electrical measuring instrument (meter) 4. Furthermore, the reference electrode 5c is manufactured by coating the conductive carbon with silver/silver chloride by printing or the like. The working electrode Sa is formed over the whole width of the carrier 3 composed of the resin sheet, and the reference electrode 5c and a counter electrode 5b are placed on the left end side and the right end side respectively of the carrier 3 of the electrical internal structure on the rear side (downstream side) of the working electrode 5a. Each of the electrode portions 5a to 5c is drawn out from the electrically conductive portion 7 and connected to the connecting portion 12 on the rear downstream side. Then, the electrically conductive portion 7 for transferring electric current, and the connecting portion 12 for connecting the sensor to the electrical measuring instrument 4 are formed, and furthermore, in the counter electrode 5b, the conductive carbon is coated with silver/silver chloride by printing or the like to manufacture the supporting body 2. In FIG. 1, the electrode portion 5 and the connecting portion 12 for connecting to the electrical measuring instrument 4 are printed on the carrier 3 made of a synthetic resin or the like, and the electrode (working electrode 5a and counter electrode 5b) 5, the electrically conductive portion 7, and the connecting portion 12 for connecting to the meter are formed by printing the conductive carbon. Silver/silver chloride is applied to the reference electrode 5c by printing.

Examples of a materials for a conductive carbon particle paste to be printed on the supporting body 2 include Ketjen black, graphene, carbon nanotube, fullerene, and the like. In terms of cost, Ketjen black is suitable. Silver/silver chloride to be printed on the reference electrode 5c is excellent in a coating face and adhesiveness because a paste composed of silver chloride crystal fine particles is printed. The carrier 3 composed of the resin sheet only needs to be a sheet made of various resins. For example, although polystyrene having a thickness of 0.1 to 0.5 mm was used, a substrate-like one may be used as long as the electric circuit and the pads can be laminated thereon.

(Carrier: Electric Circuit Carrier)

In the supporting body 2 with the electric circuit printed thereon used in the present invention, the electrode portion 5 and the wiring are constructed on the carrier 3. The carrier 3 constituting the electrodes and wirings can be manufactured by: printing the conductive carbon on the three electrode portions 5 (5a, 5b, 5c), the electrically conductive portion 7 for transferring the electric current from these electrodes, and the connecting portion 12 for connecting to the electrical measuring instrument 4 for measuring the electric current values of the electrode portions; printing silver/silver chloride on the reference electrode; and coating three electrically conductive portion 7 drawn from the electrode portions 5 (5a, 5b, 5c) with the electrical insulator 9 (urethane resin, polyamide resin, polyether resin, phenol resin, etc.) by printing or the like.

(Marker)

The marker used in the present invention may be any electrolyzable metal particles (fine particles, colloid particles, quantum dots, of gold, platinum, silver, copper, rhodium, palladium, or the like), and a diameter of the particles may be 20 nm to 100 nm. Gold colloid particles having diameters of 40 nm to 60 nm are particularly preferable. This gold colloid particles can be manufactured by a common method, e.g., by dripping a trisodium citrate aqueous solution into a heated hydrogen tetrachloroaurate (III) aqueous solution and stirring the mixture.

(Flow Passage Portion Fiber Pad)

The flow passage portion fiber pad 10 used in the present invention is a nonwoven fabric made of a fibrous fine fiber, and a material of the flow passage portion fiber pad 10 only needs to be a thin nonwoven fabric with strong capillary force formed of a glass fiber, a resin fiber, a carbon fiber, a natural fiber, or the like. A glass fiber having a thickness of 0.3 to 1.0 mm is particularly suitable. The flow passage portion fiber pad 10 causes the antigen or antibody in the sample solution to flow in a lateral direction while reacting with the antigen or antibody bonded with the marker in the conjugation pad, and leads it to the reaction area (on the working electrode) 5a.

(Flow Rate Control Pad)

The flow rate control pad 15 used in the present invention is a nonwoven fabric made of a fibrous fine fiber, and a material of the flow rate control pad 15 is a thin nonwoven fabric with weak capillary force formed of a glass fiber, a resin fiber, a carbon fiber, a natural fiber, or the like. Compared to the flow passage portion fiber pad 10 with a thickness of 0.3 to 1.0 mm made of a glass fiber, a dense natural fiber nonwoven fabric having a thickness of 0.1 to 0.7 mm is more suitable for the flow rate control pad 15.

The flow rate control pad 15 according to this embodiment is located at the position of the electrode portion (working electrode, counter electrode, and reference electrode on which silver/silver chloride is printed) 5. Then, flow rate control protruding portions 27 located on an upper case back face 22b of the cassette case 31-1 or 31-2 press the flow rate control pad 15 from above at two or more positions or at one position over the entire surface to control the flow of the test substance.

In an embodiment, a flow rate control protruding portion 27a on the upstream side is placed corresponding to the position of the working electrode 5a, and a flow rate control protruding portion 27b on the downstream side is placed corresponding to the positions of the reference electrode 5c and the counter electrode 5b. In other words, two positions on the front (upstream) side and the rear (downstream) side of the flow rate control pad 15 are pressed at the position of the electrode portion 5, so that the flow rate control protruding portions 27 press the working electrode side 5a, the reference electrode 5c and the counter electrode 5b between the two positions (H1-H2) via the flow rate control pad 15 (FIG. 5). Note that the flow rate control pad 15 of the electrochemical lateral flow immunosensor 2-1 or 2-2 according to the present application is not pressed by the flow rate control protruding portions 27 unless the electrochemical lateral flow immunosensor 2-1 or 2-2 is accommodated in the cassette case 31-1 or 31-2.

(Method for Manufacturing Electrochemical Lateral Flow Immunosensor)

The method for manufacturing the immunosensor 2-1 according to the present invention includes: applying an adhesive on the supporting body 2 excluding the three electrode portions 5; fixing the most downstream lower face corresponding to the position of the flow rate control pad 15 excluding the three electrode portions 5 to the supporting body 2; laminating the downstream lower face of the flow passage portion fiber pad 10 onto the upper face of the flow rate control pad; fixing the remaining part of the lower face on the supporting body with the adhesive; laminating a part of the downstream lower face of the conjugation pad 11 onto the upstream upper face of the flow passage fiber pad 10; laminating the downstream lower face of the sample pad 8 onto the upstream upper face of the conjugation pad 11; and fixed the remaining part of the lower face on the supporting body with the adhesive.

The method for manufacturing the immunosensor 2-2 according to the present invention includes: applying an adhesive on the supporting body 2 excluding the three electrode portions 5; fixing the lower face of the flow passage portion fiber pad 10 excluding the electrode portions on the supporting body with the adhesive; laminating the lower face of the flow rate control pad 15 onto the upper face of the electrode portion area of the flow passage portion fiber pad 10; fixing the most downstream lower face on the supporting body 2 with the adhesive; laminating a part of the most downstream lower face of the conjugation pad 11 onto the upstream upper face of the flow passage fiber pad 10; laminating the downstream lower face of the sample pad 8 onto the upstream upper face of the conjugation pad 11; and fixing the remaining part of lower face on the supporting body with the adhesive.

Each of the electrode portions 5 on the supporting body can be printed in various ways. For example, in screen printing, a printing plate that can print conductive carbon or silver/silver chloride at a time in a shape that many (e.g., 50 or more) electrode portions 5 are continuously arranged for one measurement is prepared as e.g., a supporting body on which 50 or more electrodes are continuously printed, so as to manufacture the sensor as a continuous body in which a part of each material required for the electrochemical lateral flow immunosensor according to the present invention is laminated on each other.

Examples of the mass production method include an automatic manufacture apparatus for immunochromatographic test strips commercially available from BioDot, Inc. In this apparatus, elongate materials are pasted, and a marker is applied on the conjugation pad 11 that is one of these materials, is dried, and is cut into pieces with a width corresponding to that of each immunosensor. Thereby the electrochemical lateral flow immunosensor 1 of this patent can be mass-produced and supplied at a lower cost.

As the manufacture method, a plurality of pads 8, 10, 11, 13, 15 and 16 are previously connected together and then collectively pasted onto the electrode layer, resulting in more efficient manufacture. In addition, the flow rate control protruding portions 27a and 27b can be formed in accordance with the shapes of the electrode portions 5a, 5b, and 5c so as to press the pads 8, 10, 11 and the like and control the flow pattern including the flow rate and/or volume of the sample solution.

(Measurement Principle)

The measurement method using the sensor 2-1 or 2-2 according to the present application (test method as an example of antigen measurement) will be explained below.

Figure 7:
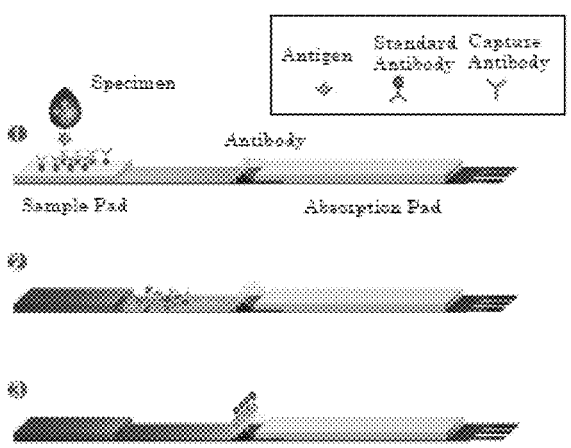
FIG. 7 is a diagram illustrating an example of the principle for testing a sample solution in the electrochemical lateral flow immunosensor according to the embodiment.

As illustrated in FIG. 7, a specimen (containing an antigen to be measured) is dripped onto the sample pad 13 impregnated with an antibody bonded to a gold colloid (1 of FIG. 7), then the gold colloid-bonded antigen and the antigen (to be measured) cause an antigen+antibody reaction while flowing over the flow passage (2 of FIG. 7), the reactant binds to the capture antibody immobilized on the electrode portion (surface of the supporting body) 5 located in advance of the sample pad 13 to form a sandwich structure, and unreactants (excess antibody bonded to the gold colloid) are captured by the absorption pad 16 (3 of FIG. 7). Then, an electrolytic solution (saline or the like) is dripped onto the flow passage portion fiber pad 10 from an electrolytic solution hole 29 and made to reach the part of the "gold particle-bonded antibody+antigen+capture antibody (immobilized on the electrode portion 5)" in 3 of FIG. 7, the unreacted gold colloid-bonded antibody fed excessively relative to the antigen amount in the specimen is removed by washing, then the part of the connecting portion 12 on the electrode portion printed on the supporting body 2 is connected to the electrical measuring instrument (meter) 4, to which a certain voltage is applied, a generated reduction current of the gold particles is measured to quantify a concentration of the measurement subject in blood.

According to the first embodiment, the antigen in the specimen and the gold colloid-bonded antibody flow during the antigen-antibody reaction and closely approach the capture antibody immobilized on the electrode portion (working electrode), so that the almost all the antigens in the specimen bind to the capture antibody while flowing away on the electrode.

Then, the metal fine particles in an amount corresponding to the test substance (antigen or antibody) in the sample solution are gathered on the working electrode 5a by the flow rate control pad 15 placed on the upper face of the electrode portion 5 position, the metal fine particles are electrochemically oxidized, then an electric current value generated during the electrochemical reduction of the oxidized metal is detected by the electrode portion 5, and the presence or concentration of the test substance is measured on the basis of the electric current value.

In other words, for example, the antigen or antibody in the specimen in the antigen-antibody reaction is specifically reacted with the antibody or antigen bonded to the metal fine particle, the metal fine particles in an amount corresponding to the amount of the test substance are gathered near the surface of the working electrode, the metal constituting the metal fine particles is electrochemically oxidized, then the reduction current value in the reduction of the oxidized metal is measured. Since the intensity of the obtained reduction current represents the amount of the metal gathered near the working electrode, the antigen or antibody in the test substance can be quantified or detected on the basis of this intensity. Herein, it is important that the metal fine particles are electrochemically oxidized in a state that the metal fine particles are gathered near the surface of the working electrode. Thus, the lower face of the electrode portion area of the flow rate control pad or the flow passage fiber pad, which is placed using no adhesive, should be directly brought into close contact with the supporting body. Thereby, all the metal fine particles involved in the reaction with the test substance can be involved in electron donation/acceptance with the surface of the working electrode, resulting in a highly sensitive and precise measurement of the test substance.

[Production of Electrochemical Lateral Flow Immunosensor for Quantifying CRP]

(Preparation of Anti-CRP Monoclonal Antibody Solution)

CRP antibodies used in the following tests are two anti-human CRP monoclonal antibodies (No. 8 and No. 5) manufactured by Immuno Probe Co., Ltd. Solutions were prepared by diluting each antibody to a concentration of 5 mg/ml with 10 mM-Tris buffer.

(Example of CRP Immunosensor Preparation)

1) In preparing the carrier 3, the working electrode 5a, the counter electrode 5b, the reference electrode 5c, the electrically conductive portion 7, and the connecting portion 12 in shapes as illustrated in FIG. 1 and FIG. 2 were screen-printed on a supporting body (transparent polystyrene by Lohmann Precision Die Cutting LLC) 2 using an electrically conductive carbon (Ketjen black, manufactured by LION SPECIALTY CHEMICALS CO., Ltd.), then silver/silver chloride (manufactured by BAS Inc.) was printed on the reference electrode 5c, and further an electrical insulator (urethane resin) was screen-printed on the electrically conductive portion 7.

2) In preparing the sample pad 8, a cellulose fiber pad (manufactured by Ahlstrom-Munksjö Oyj) was used as the sample pad. The sample pad 8 can have many functions of: sucking up the sample and delivering the sample to a conjugate release area or an analytical membrane at a uniform and constant rate; steadily preventing the sample from overflowing from the device; filtrating the particles and cells from the sample; impregnating the sample with chemical substances to modify the sample; and the like.

3) In preparing the CRP monoclonal antibody-labelled gold colloid particles, 1.0 ml of 1.1% hydrogen tetrachloroaurate (III) tetrahydrate (manufactured by Tanaka Kikinzoku Kogyo K.K.) aqueous solution and 2.44 ml of aqueous solution prepared by diluting $K_2CO_3$ manufactured by FUJIFILM Wako Pure Chemical Corporation (part No. 162-03495) to 10 mM were added to 99 ml of distilled water and mixed. The mixture was heated at 50° C. for 3 minutes, and 1.0 ml of aqueous solution, in which sodium citrate (part No. 191-01785, manufactured by FUJIFILM Wako Pure Chemical Corporation) was diluted to 1.1%, was added to the mixture, which was boiled for 11 minutes and then cooled in distilled water ice to prepare a gold colloid with an average particle diameter of 40 nm.

To 1 ml of the above gold colloid solution, 1 ml of CRP antibody solution prepared by diluting an anti-human monoclonal antibody (No. 8, manufactured by Immuno Probe Co., Ltd.) to 0.5 mg/ml with 10 mM Tris buffer was added, mixed and stirred, then the mixture was allowed to stand at room temperature for 60 minutes, to which 10% bovine serum albumin solution was further added and dispersed with ultrasonic waves The mixture was allowed to stand at room temperature for 5 minutes and centrifuged by a cooled centrifuge, from which a supernatant was removed to obtain a precipitate. To this precipitate, 10 ml of 10% bovine serum albumin solution was added again and dispersed with ultrasonic waves, an absorbance (OD) of this solution was measured at a wavelength of 520 nm, and a concentration of this solution was adjusted such that the absorbance (OD) was about 9 to prepare a CRP monoclonal antibody-labelled gold colloid solution.

4) Preparation of Conjugation Pad 11

GLASSFIBER DIAGNOSTICS PAD manufactured by EMD Millipore Corporation was impregnated with the CRP monoclonal antibody-labelled gold colloid particles (conjugate) solution prepared in the above 3) until saturation, and then the pad was dried in a lyophilizer overnight to prepare the conjugation pad 11. During a storage period, the conjugation pad 11 preserves the conjugates and maintains the detectability, and efficiently releases these conjugates while the sample moves through the pad.

5) Immobilization of Anti-Human Monoclonal CRP Antibody on Working Electrode

An anti-human monoclonal CRP antibody (No. 5, manufactured by Immuno Probe Co., Ltd.) was diluted with 10 mM Tris buffer, and 4 µl of the diluted solution was placed on the working electrode 5a and allowed to stand in a refrigerator overnight. Then, the remaining antibody solution was blown off by an air gun, and the anti-human monoclonal CRP antibody was immobilized on the working electrode.

6) Blocking on Electrode Portion

To block proteins and the like not to be measured in the sample solution (sample) from being adsorbed into the three electrode portions 5, 10 µl of boric acid aqueous solution containing 2.5% casein (pH 8.5) was placed on each of the three electrode portions (working electrode 5a, counter electrode 5b, reference electrode 5c), which was allowed to stand at room temperature in normal humidity for 1 hour, and then the remaining solution was blown off by an air gun.

7) Preparation of Electrochemical Lateral Flow Immunosensor

Figure 3:
FIG. 3 is plane views and a three-dimensional view illustrating an upper case of an accommodation cassette case that accommodates the lateral flow immunosensor according to the embodiment.
Figure 3:
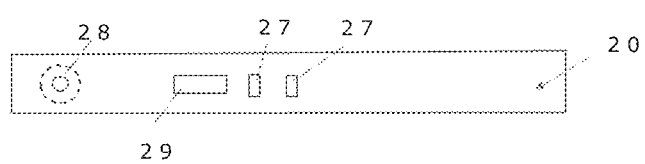
Figure 3:
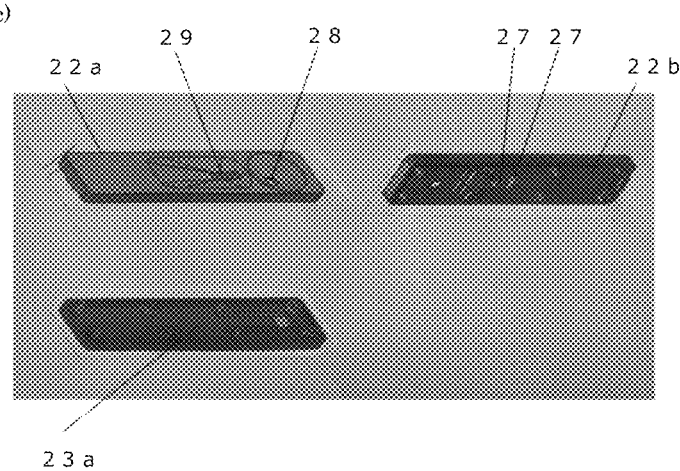

A flow passage portion fiber pad (glass fiber pad, part No. 8964, manufactured by Ahlstrom-Munksjö Oyj) 10, the conjugation pad 11 prepared in above 4), and a sample pad (glass fiber pad, part No. 0238, manufactured by Ahlstrom-Munksjö Oyj) were placed and attached in this order onto the supporting member 2 in which a viscosity-producing agent was applied on a plastic. On the other hand, a flow rate control pad (cellulose long fiber nonwoven fabric, part No. SA28G, manufactured by Asahi Kasei Corporation) 15 and an absorption pad (cellulose fiber pad, part No. 0270, manufactured by Ahlstrom-Munksjö Oyj) 16 were placed and attached in this order onto the upper ends of the three electrode portions 5 on the downstream side of the flow passage portion fiber pad 10. The structure in which the respective components were superimposed in this way was cut out with a width of the printed electrode portion unit to prepare the electrochemical lateral flow immunosensor 1. This lateral flow immunosensor 1 according to the present invention was made in a form of a test device with an exclusive plastic housing when used in measurement. In other words, as illustrated in FIG. 3 (a) and (b), the electrochemical lateral flow immunosensor 1 is configured to be plugged into the cassette case 30 having a feeding hole 29 for feeding the sample solution and a washing liquid on the upstream side.

Figure 4:
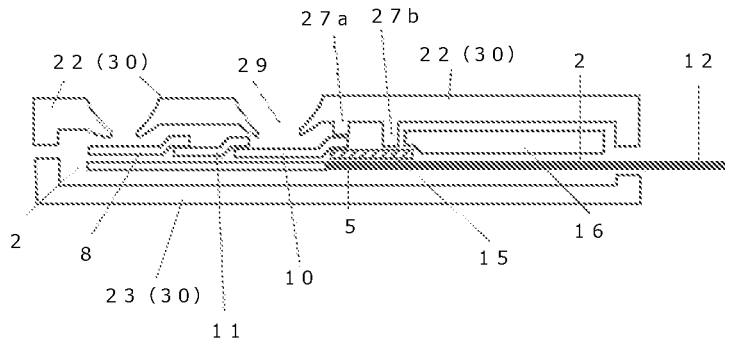
FIG. 4 is side views illustrating two different states ((a) and (b)) in which the electrochemical lateral flow immunosensor according to the embodiment is accommodated in a cassette, and illustrating a structure in which a certain pressure is applied onto the flow rate control pad 15 from the back face of the upper case to contribute to control of the flow rate. The protruding portions 27 are placed on the flow rate control pad 15, and the number of the protruding portions 27 may be one for pressing the whole face, or two or three or more for pressing both ends, in short, the number is not limited as long as the aforementioned flow rate control can be achieved.
Figure 4:
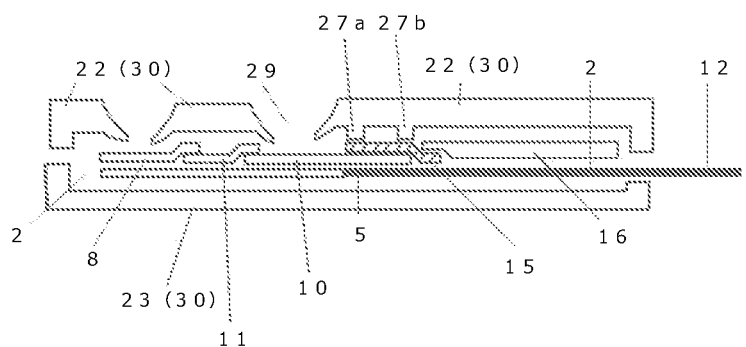

In FIG. 4 (a) and (b), the electrochemical lateral flow immunosensor 1 is configured to be housed in the cassette case 30. In FIG. 4 (a), the flow rate control pad 15 is brought into close contact with the electrode portion 5. On its upstream side, a lower layer of a downstream end of the flow passage portion fiber pad 10 is laminated onto an upper layer of an upstream end of the flow rate control pad 15. On its downstream side, a lower layer of an upstream end of the absorption pad 16 is laminated so that the sample solution is led to the absorption pad 16. Thus, the flow rate control pad 15 is brought into close contact with the electrode portion 5 and pressed by the front (upstream) pad 11 and the back (downstream) pad 16, and thereby the flow rate of the sample solution on the flow rate control pad 15 can be reduced.

In FIG. 4 (b), the flow passage portion fiber pad is laid over the surface of the electrode portion 5, and the flow rate control pad 15 is laminated onto and brought into close contact with the electrode portion of the flow passage portion fiber pad 10. On its downstream upper face passing through the electrode portion area, the upstream end under layer of the absorption pad 16 is laminated so that the sample solution is led to the absorption pad 16. Thus, by laminating the flow rate control pad 15 onto the upper layer at the electrode portion of the flow passage portion fiber pad 10, the flow rate of the sample solution can be reduced, and by laminating a part of the downstream side of the flow rate control pad 15 onto the upstream end portion of the absorption pad 16, the sample solution can be moved.

In this way, a part of the upstream side or downstream side of the flow rate control pad 15 is laminated with the other pad, so that the sample solution can be moved to the surface of the electrode 5, and the flow pattern can be controlled such that the pads are in close contact with the electrode portion while the volume and the flow rate of the sample solution is constantly kept near the surface of the electrode portion 5.

8) Cartridge Unit of Lateral Flow Immunosensor

The cassette case 30 that is a cartridge unit for accommodating the lateral flow immunosensor 1 according to the present invention is composed of the upper case 22 and a lower case 23 and formed by molding a material which is a resin such as polypropylene, polyester, polystyrene, and acryl. The immunosensor 1 according to the present invention at a predetermined position in the lower case 23 is covered with the upper case 22, and both cases are fitted into each other by pressing them. The flow rate control protruding portions 27 are formed on an inner wall on the upper case back face 22b. The flow rate control protruding portions 27 press the flow rate control pad 15 from above to control the flow rate, and the number of the protruding portions 27 may be two as in this embodiment but not limited thereto, i.e., the number may be one or plural number. In addition, the cassette case 31-1 or 31-2 had a sample hole 28 and the washing/electrolytic solution hole 29 (FIG. 3 (a)), and the flow rate control protruding portions 27 for controlling the function of the flow rate control pad 15 were placed on the upper case back face 22b such that the flow rate control protruding portions 27 were located on the flow rate control pad 15 (FIG. 3 (b)). Although the washing can be performed by feeding the washing/electrolytic solution to the sample hole 28, the feeding from the washing/electrolytic solution hole/electrolytic solution hole 29 that is closer to the electrode portion 5 is superior in washing efficiency and also allows more efficient measurement in the feeding of the electrolytic solution.

FIG. 5 (a) and (b) are diagrams illustrating a positional relationship between the flow rate control protruding portions 27 on the cassette upper case back face 22b and the electrode portion 5 of the electrochemical lateral flow immunosensor 2-1 or 2-2. FIG. 5 (a) illustrates an example in which the flow rate control protruding portion 27a on the upstream side is placed on the working electrode 5a of the electrode portion 5, and the flow rate control protruding portion 27b on the downstream side is placed on the counter electrode 5b (or reference electrode 5c) of the electrode portion 5. An area between the upstream and downstream flow rate control protruding portions 27a and 27b that press the flow rate control pad 15 is defined as a reaction area H1-H2 so as to control the flow pattern including the flow rate and/or flow volume of the sample solution.

In FIG. 5 (b), the area between the upstream and downstream flow rate control protruding portions 27a and 27b that are placed above the working electrode 5a of the electrode portion 5 is defined as the reaction area H1-H2, and the flow pattern including the flow rate and/or flow volume of the sample solution is controlled. Furthermore, the flow rate control protruding portion 27b may be placed on the counter electrode 5b (or reference electrode 5c) of the electrode portion 5.

In this way, when the upstream side or downstream side of the flow rate control pad 15 is pressed by the flow rate control protruding portions 27a and 27b, the volume and the flow rate of the sample solution in a predetermined region H1 to H2 of the flow rate control pad 15 can be controlled in a certain range. In addition, using conventional printing technique and lamination technique, efficient manufacture can be achieved by a step of printing an electrical wiring structure with conductive carbon on the supporting body composed of the resin sheet and printing silver/silver chloride on the conductive carbon, a step of immobilizing an antibody or antigen on the surface of the working electrode, and a step of laminating the plurality of pads 8, 11, 10, 15 and 16 on the supporting body. The flow rate control protruding portions 27a and 27b may be placed in a sloping configuration above the electrode portion 5 (see FIG. 9 (b)).

FIG. 8 illustrates another example of this embodiment, in which flow rate control protruding portions (P1 to P3) 27c are placed at positions other than the flow rate control protruding portions 27a and 27b, and they press the pads 8, 11, 10, 15, and 16 located under the protruding portions, and the electrode portion 5, the electrically conductive portion 7 and the like located under the pads so as to control the flow pattern including the flow rate and the flow volume of the sample solution.

As illustrated in FIG. 9 (a) and (b), it is preferable that pad pressers P1 to P3 (27c) are provided on the case back face 22b of the cassette case 30. The pad presser P1 is intended to press the absorption pad 16. When the absorption pad 16 absorbs liquid and becomes soft, the pad is likely to deviate and the sample solution is likely to flow back, and therefore the presser P1 for pressing the absorption pad is provided for the purpose of preventing the deviation and backflow. In addition, the flow rate control protruding portions P2 and P3 are provided for the purpose of preventing warp and deviation of the sample pad 8, the conjugation pad 11, the flow passage portion fiber pad 10, and the flow rate control pad 15. These flow rate control protruding portions P1 to P3 may be configured in a sloping configuration (FIG. 9 (b)) so as to define the flow of the solution to be a sloping shape (in an inclined plane) and stabilize the flow rate. These flow rate control protruding portions P1 to P3 may be configured to press the electrode portion 5 from above in the same way as for the aforementioned flow rate control protruding portions 27a and 27b.

Example 1

The electrochemical lateral flow immunosensor 1 prepared by the aforementioned preparation method was used for a CRP quantitative test.
(Test Method)
(1) Sample
A CRP reference serum (manufactured by Kanto Chemical Co., Inc.) was diluted with physiological saline (containing 1% bovine serum albumin) to prepare samples with CRP concentrations of 15 ng/ml, 90 ng/ml, and 210 ng/ml. Also, a diluted solution with CRP concentrations of 0 mg/dl was prepared as a sample.
(2) Procedure
Fifty five µl of each sample prepared in the above (1) was dripped into the sample feeding hole 29 of the electrochemical lateral flow immunosensor 1. After 3 minutes, the sample was dripped into a hole (also serving as the electrolytic solution feeding hole) 29 for feeding a washing solution/electrolytic solution (2M-NaCl containing 0.05% surfactant Tween 20) and washing solution, and after 3 minutes, electrolytic currents (µA) generated corresponding to the CRP concentrations were measured 12 times for each of the four sample solutions with four concentrations presented in Table 1. However, the sample solution with zero concentration was measured 10 times.
(Test Results)

Test results are presented in Table 1. The results of the quantitative measurement were as follows; at a CRP concentration of 15 ng/ml, a mean value was 1.154 µA, a CRP concentration per 1 µA was 13.00 ng/ml, and a concentration corresponding to its standard deviation of 0.282 µA was 3.666 ng/ml; and at a CRP concentration of 90 ng/ml, a mean value was 3.230 µA, a CRP concentration per 1 µA was 27.86 ng/ml, and a concentration corresponding to its standard deviation of 0.420 µA was 11.70 ng/ml. Furthermore, the results of the quantitative measurement showed accuracy, in which, at a CRP concentration of 210 ng/ml, a mean value was 3.993 µA, a CRP concentration per 1 µA was 52.59 ng/ml, a concentration corresponding to its standard deviation of 0.707 µA was 37.18 ng/ml.

| The unit of current is µA. | | | | |
|---|---|---|---|---|
| | 0 ng/ml | 10 ng/ml | 90 ng/ml | 210 ng/ml |
| 1 times | 0.142 | 1.039 | 3.283 | 3.891 |
| 2 times | 0.038 | 0.910 | 3.495 | 3.040 |
| 3 times | 0.100 | 1.286 | 3.360 | 3.632 |
| 4 times | 0.083 | 1.488 | 3.994 | 4.170 |
| 5 times | 0.021 | 1.206 | 2.862 | 4.839 |
| 6 times | 0.041 | 0.790 | 2.709 | 5.172 |
| 7 times | 0.126 | 1.299 | 3.704 | 4.555 |
| 8 times | 0.108 | 1.073 | 3.503 | 2.704 |
| 9 times | 0.054 | 0.766 | 2.870 | 3.751 |
| 10 times | 0.100 | 1.678 | 2.623 | 4.468 |
| 11 times | | 0.997 | 3.812 | 3.727 |
| 12 times | | 1.402 | 3.203 | 3.982 |
| mean value | 0.081 | 1.154 | 3.230 | 3.993 |
| standard deviation | 0.041 | 0.282 | 0.420 | 0.707 |

As described above, the examples of the monoclonal antibodies have been mainly explained in this embodiment.

However, the present invention can also be applied to polyclonal antibodies. In the manufacturing method, it is also possible to adopt a configuration in which parts where the adhesive is applied and parts with no adhesive (electrode portions) are previously separated, and the adhesive is applied on the pads 10, 11, 15, and 16, and then the pads are placed on the supporting body 2 having electrical internal structure such as electrodes and wiring. Furthermore, when the cassette case 30 is used, the cassette case 30 can press the pads and thus the sensor can be manufactured using no adhesive.

DESCRIPTION OF REFERENCE NUMERALS

1 Electrochemical lateral flow immunosensor
2 Supporting body (in which electrodes are printed on the carrier 3)
2-1, 2-2 Electrochemical lateral flow immunosensor
3 Carrier (having electrical internal components such as electrodes and wiring)
4 Electrical measuring instrument (meter)
5 Electrode portion
5a Working electrode
5b Counter electrode
5c Reference electrode
6 Electrical circuit
7 Electrically conductive portion
8 Sample pad
9 Electrical insulator
10 Flow passage portion fiber pad (flow passage membrane)
11 Conjugation pad
12 Connecting portion
13 Sample hole (sample solution feeding hole)
14 Control portion
15 Flow rate control pad
16 Absorption pad
17 Measurement of reduction current of metal fine particles on the electrode
22 Upper case
22a Upper case upper face
22b Upper case back face
23 Lower case
23a Lower case back face
27a, 27b, 27c Flow rate control protruding portion
27c Pad presser
28 Sample hole
29 Washing solution/electrolytic solution hole
30 Cassette case
31-1, 31-2 Cassette case (cartridge) for accommodating the lateral flow immunosensor
P1 to P3 Flow rate control protruding portion

The invention claimed is:

1. A method for manufacturing an electrochemical lateral flow immunosensor, wherein:
an electrode portion consisting of a counter electrode obtained by printing a conductive carbon on a supporting body composed of a resin sheet so as to be opposite to a working electrode printed with a conductive carbon, and a reference electrode obtained by printing silver/silver chloride; and a connecting portion connected to an electrical measuring instrument for measuring a value of an electric current are provided on a supporting body composed of a resin sheet; and
a flow passage portion fiber pad is on the supporting body, the flow passage portion fiber pad being configured to transfer an antibody or antigen in a sample solution and an antibody or antigen bonded to a marker composed of metal fine particles toward the working electrode while reacting them;
a flow rate control pad is on the electrode portion, which is connected to the flow passage portion fiber pad and configured to control a flow pattern including a flow rate and/or volume of the sample solution such that a reactant in the sample solution and a capture antibody or antigen immobilized on the working electrode cause an antigen/antibody reaction;
the flow passage portion fiber pad is on the flow rate control pad, or the flow rate control pad is on the electrode portion via the flow passage portion fiber pad, and
flow rate control pad is configured to control the flow pattern including the flow rate and/or volume of the sample solution at a position of the electrode portion and configured to electrochemically detect an amount of the metal fine particles corresponding to an amount of the antigen or antibody in the test substance, wherein the method comprises:
forming, on a supporting body composed of a resin sheet, an electrode portion consisting of a working electrode, a reference electrode and a counter electrode obtained by printing a conductive carbon, an electrically conductive portion transferring electric current of them, and a connecting portion for connecting to an electrical measuring instrument, and furthermore printing silver/silver chloride on the conductive carbon on the counter electrode;
immobilizing an antibody or antigen on a surface of the working electrode; and
placing a flow passage portion fiber pad on the support body, which transfers an antibody or antigen in a sample solution and an antibody or antigen bonded to a marker composed of metal fine particles toward the working electrode while reacting them, and placing a flow rate control pad on the electrode portion, which controls a flow pattern including a flow rate and/or volume of the sample solution such that a reactant in the sample solution and a capture antibody or antigen immobilized on the working electrode cause an antigen/antibody reaction.

2. The method for manufacturing the electrochemical lateral flow immunosensor according to claim 1, comprising a step of placing, on the supporting body:
a sample pad that absorbs a dripped sample solution;
a conjugation pad that absorbs the sample from the sample pad, and simultaneously dissolves an antibody or antigen bonded to the marker composed of a gold colloid infiltrated in the pad and dried, thereby conjugating the sample with the antibody or antigen;
the flow passage portion fiber pad that transfers the antibody or antigen in the sample and the antibody or antigen bonded to the gold colloid toward the working electrode while reacting them;
the flow rate control pad that causes an antigen/antibody reaction of a transferred reactant with the capture antibody or antigen immobilized on the working electrode to complete formation of a sandwich structure; and
the absorption pad that absorbs a reaction residue liquid of the sample solution.

3. The method for manufacturing the electrochemical lateral flow immunosensor according to claim 1, wherein:

the electrochemical lateral flow immunosensor further comprises a sample pad, a conjugation pad, and an absorption pad as pads:
a downstream part of the sample pad is laminated onto a part of an upstream upper face of the conjugation pad, and a lower face of the sample pad is fixed with an adhesive on the support body;
a downstream part of the conjugation pad is laminated onto a part of an upper face of the flow passage portion fiber pad, and a lower face of the conjugation pad is fixed with the adhesive on the support body;
a working electrode/counter electrode/reference electrode part, which is a downstream part, of the flow passage portion fiber pad is laminated onto a part of an upstream upper face, and a lower face of the flow passage portion fiber pad is fixed with the adhesive on the support body;
an upstream part of the flow rate control pad is laminated onto a part of a downstream upper face of the flow passage portion fiber pad, and a lower face of the flow rate control pad is brought into close contact with (but not fixed with the adhesive to) the three electrodes, i.e., the working electrode, the counter electrode, and the reference electrode; and
the absorption pad is laminated onto a part of an upstream lower face of the flow rate control pad, and a lower face of the absorption pad is fixed with the adhesive on the support body.

4. The method for manufacturing the electrochemical lateral flow immunosensor according to claim 3, wherein:
the upstream part of the flow rate control pad is laminated onto a part of the lower face of the flow passage portion fiber pad, and the lower face of the flow rate control pad is brought into close contact with (but not fixed with the adhesive to) the three electrodes, i.e., the working electrode, the counter electrode, and the reference electrode; and
a part of an upstream lower face of the absorption pad is laminated onto a downstream upper face of the flow rate control pad.

5. The method for manufacturing the electrochemical lateral flow immunosensor according to claim 1, wherein:
the upstream part of the flow rate control pad is laminated onto a part of the lower face of the flow passage portion fiber pad, and the lower face of the flow rate control pad is brought into close contact with (but not fixed with an adhesive to) the three electrodes, i.e., the working electrode, the counter electrode, and the reference electrode; and
a part of an upstream lower face of the absorption pad is laminated onto a downstream upper face of the flow rate control pad.

6. An electrochemical lateral flow immunological test method, wherein:
an electrode portion obtained by printing a conductive carbon, an electrically conductive portion obtained by printing conductive carbon transferring electric current from the electrode portion, and a connecting portion connected to an electrical measuring instrument for measuring a value of the electric current, are provided on a supporting body composed of a resin sheet;
a flow passage portion fiber pad is provided on the supporting body, which transfers an antibody or antigen in a sample solution and an antibody or antigen bonded to a marker composed of metal fine particles toward the electrode portion while reacting them;
a flow rate control pad is provided on the electrode portion, which is connected to the flow passage portion fiber pad and controls a flow pattern including a flow rate and/or volume of the sample solution such that a reactant in the sample solution and a capture antibody or antigen immobilized on the electrode portion cause an antigen/antibody reaction;
the flow passage portion fiber pad is on the flow rate control pad, or the flow rate control pad is on the electrode portion via the flow passage portion fiber pad, and
while the sample solution as a test substance containing the antigen or antibody and the metal fine particles to which the antibody or antigen against the antigen or antibody in the sample solution is bonded cause antigen-antibody reaction, the flow rate control pad placed on a surface of the electrode portion controls the flow pattern including the flow rate and/or volume of the sample solution so as to electrochemically detect an amount of the metal fine particles corresponding to an amount of the antigen or antibody in the test substance, wherein:
the upstream part of the flow rate control pad is laminated onto a part of the lower face of the flow passage portion fiber pad, and the lower face of the flow rate control pad is brought into close contact with (but not fixed with an adhesive to) the three electrodes, i.e., the working electrode, the counter electrode, and the reference electrode; and
a part of an upstream lower face of the absorption pad is laminated onto a downstream upper face of the flow rate control pad.

7. The electrochemical lateral flow immunological test method according to claim 6, wherein:
the flow rate control pad is provided over the surface of the electrode portion of the support body; and
a flow rate control protruding portion presses an upstream side and a downstream side of the flow rate control pad from above so as to control the flow pattern including the flow rate and/or volume of the sample solution in the predetermined area of the flow rate control pad.

8. An electrochemical lateral flow immunosensor, wherein:
an electrode portion consisting of a counter electrode obtained by printing a conductive carbon on a supporting body composed of a resin sheet so as to be opposite to a working electrode printed with a conductive carbon, and a reference electrode obtained by printing silver/silver chloride; and a connecting portion connected to an electrical measuring instrument for measuring a value of an electric current are provided on a supporting body composed of a resin sheet; and
a flow passage portion fiber pad is on the supporting body, the flow passage portion fiber pad being configured to transfer an antibody or antigen in a sample solution and an antibody or antigen bonded to a marker composed of metal fine particles toward the working electrode while reacting them;
a flow rate control pad is on the electrode portion, which is connected to the flow passage portion fiber pad and configured to control a flow pattern including a flow rate and/or volume of the sample solution such that a reactant in the sample solution and a capture antibody or antigen immobilized on the working electrode cause an antigen/antibody reaction;
the flow passage portion fiber pad is on the flow rate control pad, or the flow rate control pad is on the electrode portion via the flow passage portion fiber pad, and the flow rate control pad is configured to control the flow pattern including the flow rate and/or volume of the sample solution at a position of the electrode portion and configured to electrochemically detect an amount of the metal fine particles corresponding to an amount of the antigen or antibody in the test substance, wherein:

the upstream part of the flow rate control pad is laminated onto a part of the lower face of the flow passage portion fiber pad, and the lower face of the flow rate control pad is brought into close contact with (but not fixed with an adhesive to) the three electrodes, i.e., the working electrode, the counter electrode, and the reference electrode; and a part of an upstream lower face of the absorption pad is laminated onto a downstream upper face of the flow rate control pad.

9. The electrochemical lateral flow immunosensor according to claim 8, further comprising a sample pad, a conjugation pad, and an absorption pad as pads, wherein:

the flow passage portion fiber pad is placed to be continuous with the conjugation pad; and the flow rate control pad is provided on the electrode portion by lamination onto the flow passage portion fiber pad so as to complete the antigen-antibody reaction (sandwich method) on the working electrode.

10. The electrochemical lateral flow immunosensor according to claim 8, further comprising a sample pad, a conjugation pad, and an absorption pad as pads, wherein:

the flow passage portion fiber pad is placed to be continuous with the conjugation pad;

the flow rate control pad is provided on the electrode portion so as to complete the antigen-antibody reaction (sandwich method) on the working electrode; and the flow rate control pad is laminated onto a part of a downstream lower face of the flow passage portion fiber pad and is in contact with a part of an upstream lower face of the absorption pad.

11. The electrochemical lateral flow immunosensor according to claim 8, wherein the flow passage portion fiber pad is configured to move the sample solution to the electrode portion during the immunological reaction in the conjugation pad in which an antibody or antigen immunologically reactive with the antibody or antigen in the sample solution is bonded to colloidal metal fine particles, and infiltrated into the pad and dried.

12. The electrochemical lateral flow immunosensor according to claim 8, wherein the antibody or antigen immunochemically reactive with the test substance bonded to the marker and the antibody or antigen immunochemically reactive with the test substance immobilized to the surface of the working electrode recognizes different sites of the test substance.

13. The electrochemical lateral flow immunosensor according to claim 8, further comprising a cassette case for accommodating the electrochemical lateral flow immunosensor, wherein the cassette case comprises the flow rate control protruding portion configured to press the flow rate control pad from above and to control the flow by damming up, wherein:

the flow rate control pad is over the surface of the electrode portion of the support body; and a flow rate control protruding portion is configured to press an upstream side and a downstream side of the flow rate control pad from above and configured to control the flow pattern including the flow rate and/or volume of the sample solution in the predetermined area of the flow rate control pad.

14. The electrochemical lateral flow immunosensor according to claim 8, comprising a cassette case for accommodating the electrochemical lateral flow immunosensor, wherein the connecting portion is protruded outward from the cassette case, plugged into and connected to an electric current sensing portion of the electrical measuring instrument for detecting the electric current of the electrode portion, thereby configuring an electrical circuit for measuring the electric current generated on the electrode.

\* \* \* \* \*